United States Patent [19]
Walker

[11] Patent Number: 5,195,995
[45] Date of Patent: Mar. 23, 1993

[54] CONTROL VACUUM TO MEASURE GAS FLOW

[75] Inventor: Clarence L. Walker, Webster Groves, Mo.

[73] Assignee: Sherwood Medical Company, St. Louis, Mo.

[21] Appl. No.: 349,155

[22] Filed: May 9, 1989

[51] Int. Cl.$^5$ .............................................. A61M 1/00
[52] U.S. Cl. .................................................... 604/319
[58] Field of Search ............ 604/65, 66, 118, 318–322, 604/323

[56] References Cited

U.S. PATENT DOCUMENTS

| | | | |
|---|---|---|---|
| 1,885,926 | 11/1932 | Lewis . | |
| 2,378,849 | 6/1945 | Helleberg et al. | 73/290 |
| 2,381,821 | 8/1945 | Helleberg et al. | 73/290 |
| 3,363,461 | 1/1968 | Minkoff | 73/194 |
| 3,643,507 | 2/1972 | Garrett | 73/194 R |
| 3,744,306 | 7/1973 | Krueger | 73/149 |
| 3,773,211 | 11/1973 | Bridgman | 604/319 |
| 3,839,911 | 10/1974 | Zimmerman et al. | 73/194 E |
| 4,050,896 | 9/1977 | Raffel et al. | 23/230 A |
| 4,056,002 | 11/1977 | Arieh et al. | 73/194 R |
| 4,168,624 | 9/1979 | Pichon | 73/195 |
| 4,169,374 | 10/1979 | Budliger et al. | 73/194 E |
| 4,178,801 | 12/1979 | Cassell et al. | 73/195 |
| 4,289,018 | 9/1981 | Hellouin de Menibus | 73/19 |
| 4,372,336 | 2/1983 | Cornell et al. | 137/205 |
| 4,439,190 | 3/1984 | Protzmann et al. | 604/319 |
| 4,464,172 | 1/1981 | Lichtenstein | 604/65 |
| 4,626,248 | 12/1986 | Scheller | 604/319 |
| 4,654,029 | 3/1987 | D'Antonio | 604/119 |
| 4,888,003 | 12/1989 | Johnson et al. | 604/320 |

OTHER PUBLICATIONS

Fuel Gage For Sloshing Tanks; NASA Tech Briefs, Winter 1985.
Vent Time Of Vacuum Vessels; Machine Design, Mar. 20, 1986.
Determination of Small Leaks In Large Pressurized Volumes; Sensors, Sep. 1988.

*Primary Examiner*—Randall L. Green
*Assistant Examiner*—R. Clarke
*Attorney, Agent, or Firm*—Montgomery W. Smith; Richard D. Allison; Curtis D. Kinghorn

[57] ABSTRACT

A chest drainage apparatus (CDU) and method is disclosed for accurately measuring gas flow or leakage from a patient's chest cavity even at very low or near zero flow rates. The CDU has a collection chamber for receiving fluid and gas to be drained from a pleural cavity of a patient, a vacuum source for applying suction to the collection chamber and a valve for connecting the CDU to the vacuum source. A pressure transducer measures the gas pressure in the collection chamber. A microcomputer controller, responsive to the pressure measured by the pressure transducer, causes the valve to disconnect the vacuum source from the CDU when the gas pressure in the collection chamber is less than a first predetermined threshold and connects the CDU to the vacuum source when the gas pressure in the collection chamber exceeds a second predetermined threshold. The time period during which the vacuum source is disconnected from the CDU is measured as an indication of the rate of gas flow into the CDU.

7 Claims, 2 Drawing Sheets

CONTROL VACUUM TO MEASURE GAS FLOW

BACKGROUND OF THE INVENTION

The present invention relates to a novel and improved chest drainage apparatus capable of accurately measuring gas leakage or flow from a patient's chest cavity, even at very low, near zero or zero flow rates.

Devices for measuring gas flow such as flow meters and hot wire annenometers are well-known and have been used to measure the flow of both gases and liquids in a wide variety of industrial applications. Examples of such applications included (a) controlling the amount of gas added to a liquid reaction component in the production of foam materials (see U.S. Pat. No. 4,050,896 to Raffel et al.), determining the respective flow rates of gas and crude oil in the diphase mixture during a production test of a well (U.S. Pat. No. 4,168,624 to Pischon), measuring the rate of flow of air from a tank to determine the volume of dry materials in the tank (U.S. Pat. No. 3,744,306 to Krueger), and measuring the flow rate of desolubilized gas from a liquid under vacuum to determine the amount of gas remaining in the liquid (U.S. Pat. No. 4,289,018 to Hellouin De Menibus).

However, while the utility of such devices has been proven in many industrial applications, they do not accurately measure very low or zero flow rates. Accuracy at near zero or zero flow rates is very often not critical or significantly advantageous for most industrial applications, but it is highly important in other applications such as monitoring leakage of poisonous gases from storage receptacles, as well as in certain medical applications such as the measurement of gas flow or leakage from a patient's chest cavity in a chest drainage unit.

A chest drainage unit is used to suction gases and liquids from the chest cavities, or pleural cavities of patients. The pleural cavity contains both lungs, which in their normal expanded state fill the pleural cavity. Several conditions and diseases such as emphysema and various infections can cause a build up of liquid and gases around the lungs inside the pleural cavity. This causes the lungs to collapse to a volume much less than that of the pleural cavity, severely impairing breathing functions. The lungs can be re-expanded to their normal state by draining the liquid and gases from the area outside the lungs using a chest drainage unit.

Chest drainage units are also used in the treatment of patients who have air leaks in their lungs, allowing excessive amounts of air to enter the pleural cavity. The excess pressure in the pleural cavity caused by the air leaks can be relieved through evacuation of the air via a chest drainage unit.

U.S. Pat. No. 4,372,336 issued to Cornell et al. and assigned to Sherwood Medical Industries, Inc., discloses and claims a conventional chest drainage unit similar to those contemplated for use in connection with the present invention.

In measuring the air flow from a patient's pleural cavity via a chest drainage unit, the physician is most interested in the measurement of air flows near and at zero. This is because patient air leakage progresses to zero in the final stages of healing, making the precise measurement of those final flow rates very important. There is therefore presently a great need for a safe, efficient, and accurate method of measuring air flow in a chest drainage unit which is very sensitive to flows near and at zero.

OBJECTS OF THE INVENTION

It is an object of the present invention to provide an improved chest drainage apparatus that accurately calculates and displays the rate of gas leakage from a patient's pleural cavity, even when the rate of flow is very low, near or at zero.

It is a further object of the present invention to provide an improved chest drainage apparatus that accurately calculates and displays the rate of gas leakage from a patient's pleural cavity, even when the rate of flow is very low, near or at zero, without requiring either a high-gain, high-stability disposable amplifier circuit for a direct flow sensor, or a disposable mechanical vacuum regulator.

SUMMARY OF THE INVENTION

The present invention comprises a chest drainage apparatus having a collection chamber for receiving fluid to be drained from a pleural cavity, a vacuum source for applying suction to the collection chamber, and a valve means for connecting the chest drainage unit to the vacuum source. A pressure transducer measures the gas pressure in the collection chamber. Means responsive to the pressure transducer causes the valve to disconnect the vacuum source from the chest drainage unit when the gas pressure in the collection chamber is less than a first predetermined threshold and to connect the vacuum source to the chest drainage unit when the gas pressure in the collection chamber exceeds a second predetermined threshold. The time period during which the vacuum source is disconnected from the chest drainage unit is measured as an indication of the rate of flow of gas into the chest drainage unit.

DESCRIPTION OF THE PREFERRED EMBODIMENT

Figure 1:
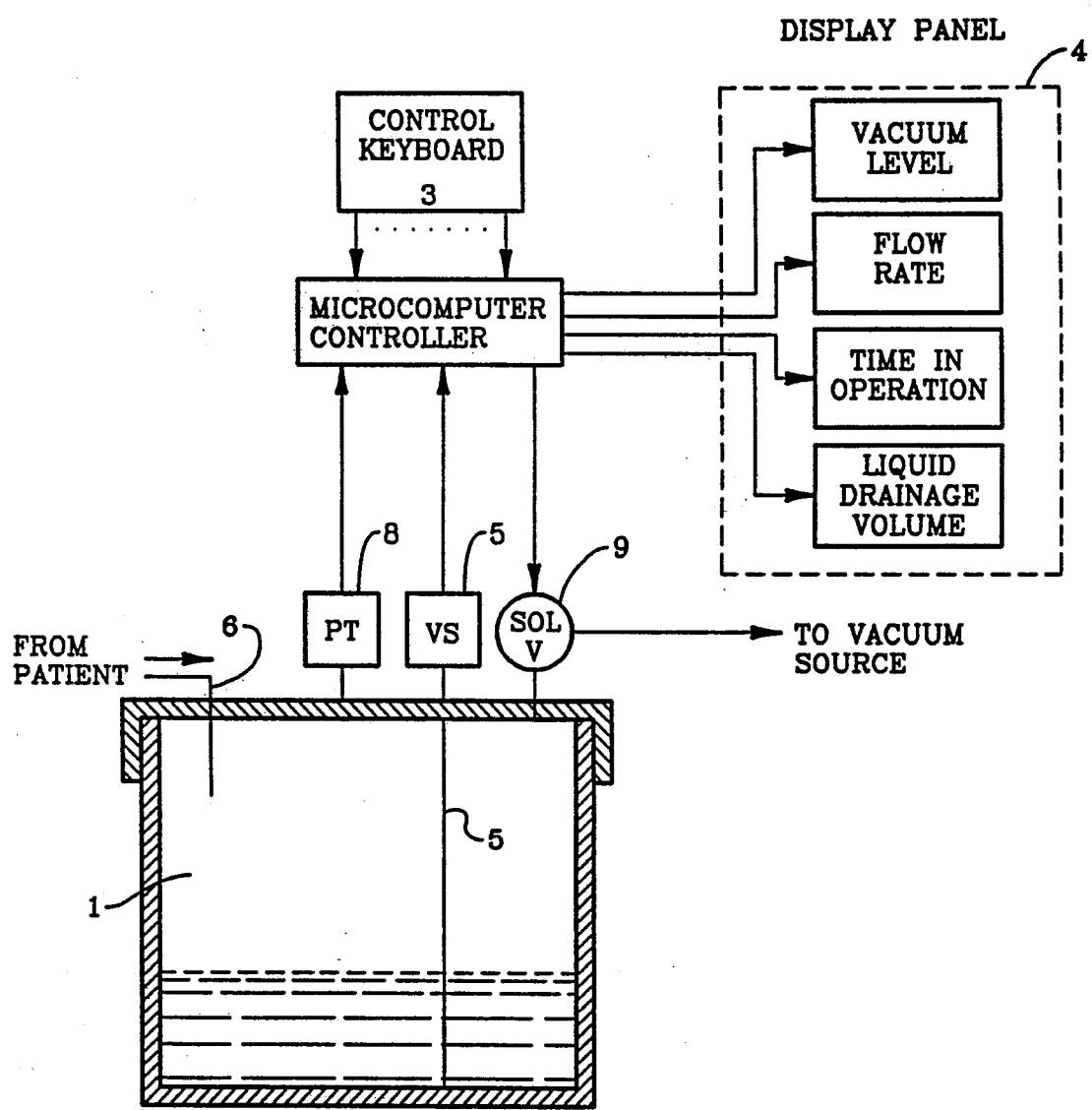
FIG. 1 shows diagrammatically the improved chest drainage apparatus of the present invention with a schematic representation of the electronic components of the unit employed in the preferred embodiment.

Referring to FIG. 1, the preferred embodiment of the improved chest drainage apparatus of the present invention comprises a collection chamber for receiving fluid to be drained from a pleural cavity. Connected to and in the nearby vicinity of the chest drainage unit are a microcomputer controller 2, a keyboard 3, and a display panel 4.

A vertically positioned liquid volume sensor 5 extends into collection chamber 1. The collection chamber 1 communicates with the patient's pleural cavity through a connecting tube 6, and with a source of suction through another connecting tube 7. There is at least one pressure transducer 8 which measures the gas pressure in the collection chamber 1.

A control valve 9 controls in an "on-off" fashion the communication between the collection chamber 1 and the vacuum source. The control valve 9 in turn is controlled by a solenoid which causes the valve to open when the solenoid is energized and close when power is removed from the solenoid, thus establishing and interrupting communication between the collection chamber 1 and the vacuum source. The microcomputer controller 2 is responsive to the pressure transducer 8 and causes the valve to close and thus disconnect the vacuum source from the chest drainage unit when the gas pressure in the collection chamber is less than or equal to a first predetermined threshold, and to close and thus connect the vacuum source to the chest drainage unit when the gas pressure in the collection chamber equals or exceeds a second predetermined threshold.

The pressure transducer 8, liquid sensor 5 and solenoid communicate electrically with the microcomputer controller 2, which is also connected to the control keyboard 3 and the display panel 4.

The rate of flow of gas from the patient's pleural cavity is calculated once per cycle. A cycle is defined as the period during which the control valve is in the off position and the vacuum source is disconnected from the collection chamber. The pressure in the collection chamber at the beginning of each cycle is equal to the first predetermined threshold and the pressure in the collection chamber at the end of each cycle is equal to the second predetermined threshold.

Figure 2:
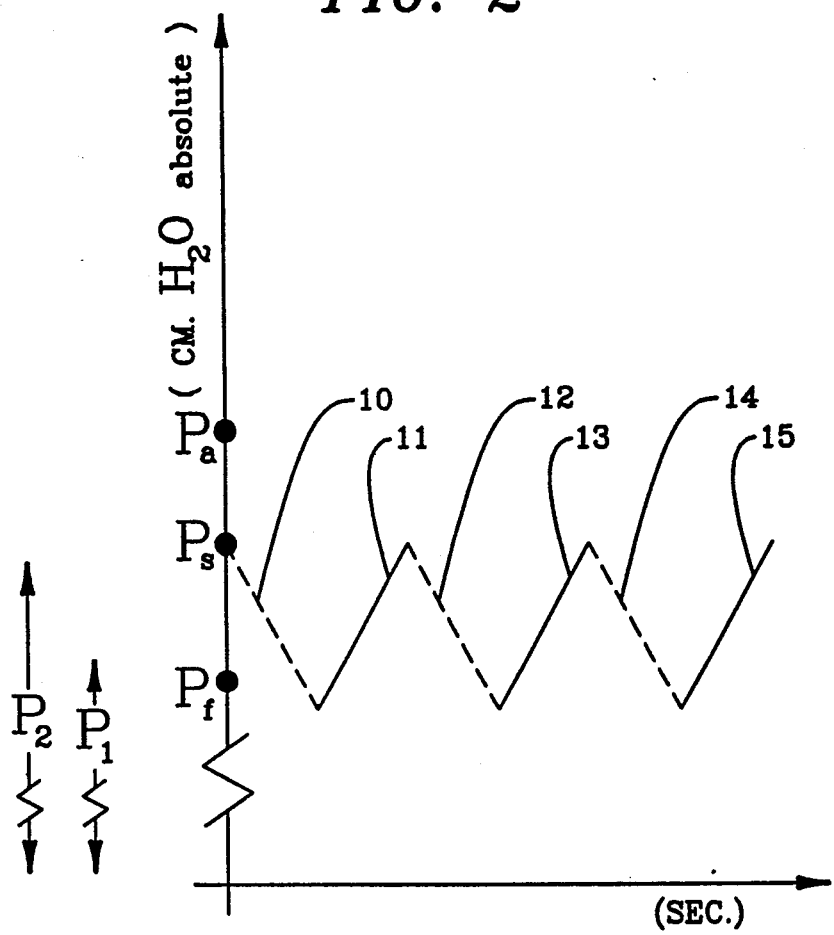
FIG. 2 is a graph of pressure versus time, showing the cyclic variation of the pressure in the collection chamber between the predetermined first and second thresholds.

Referring to FIG. 2, lines 11, 13 and 15 represent three separate cycles of the invention. $P_1$ represents the predetermined first threshold and $P_2$ represents the second predetermined threshold. Dotted lines 10, 12 and 14 represent the periods between cycles when the control valve is open and the suction source is connected to the collection chamber. The absolute values of the slopes of lines 10, 12 and 14 are proportional to the strength of the suction source. The slopes of lines 11, 13 and 15 are proportional to the rate of flow of gas into the collection chamber from the patient's pleural cavity. The first and second predetermined thresholds may be fixed to coincide with a prescribed patient suction pressure or they may be adjustable to accommodate the individual patient's needs. In either case, they may be defined absolutely or relative to ambient pressure.

Figure 3:
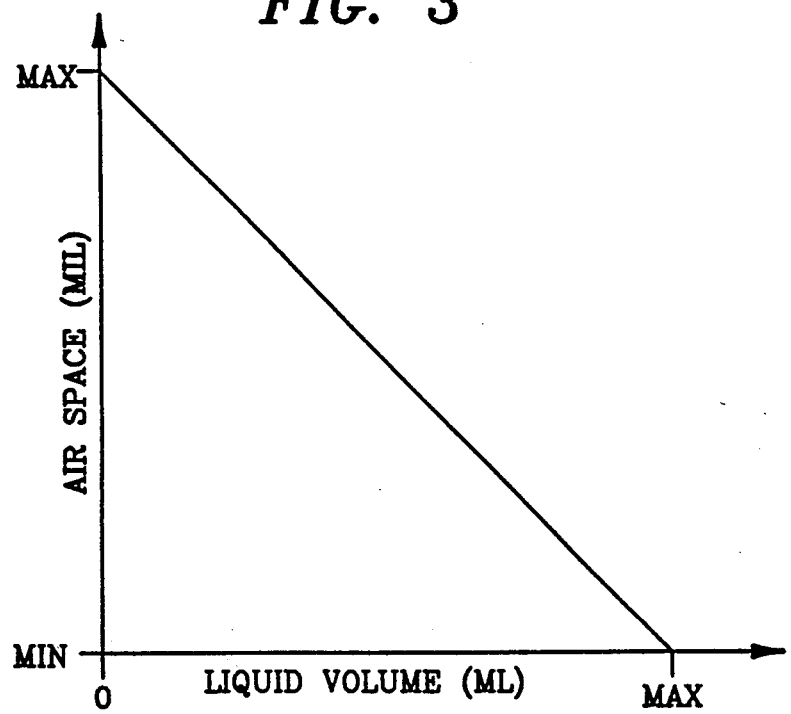
FIG. 3 is a graph depicting the linear relationship between the gas volume (air space) and the liquid drainage volume in the collection chamber.

Referring to FIG. 3, a linear relationship exists between the air space or gas volume and the liquid volume in the collection chamber 1. The sum of the air space and the liquid volume is equal to a constant, which is the total volume of the chamber. Therefore, the volume of gas in the collection chamber 1 at the beginning and end of any given cycle may be determined by measuring the liquid volume in the chamber using the liquid volume sensor 5 and subtracting the measured volume from the total volume of the chamber.

The rate of flow of gas from the patient's pleural cavity during a given cycle is determined from the volume of gas which leaked into collection chamber 1 from the patient's pleural cavity during the cycle. The volume of gas which leaked into the collection chamber during a given cycle is determined by comparing the measured gas volume at the end of the cycle with the theoretical volume obtained using Boyle's law. The measured gas volume at the end of the cycle is obtained from the total volume of the collection chamber and the volume of liquid drainage in the chamber at the end of the cycle. The theoretical gas volume based on Boyle's law is obtained from the volume of gas in the collection chamber at the beginning of the cycle and the first and second threshold pressures, i.e. the pressures of gas in the chamber at the beginning and end of the cycle. The amount by which the theoretical volume, which reflects only volume changes due to pressure changes within the chamber during the cycle, is less than the measured volume, reflects the volume of gas which entered the collection chamber during the cycle. The leakage volume is then normalized to account for ambient pressure and divided by the time which elapsed during the cycle to determine the flow rate.

When the liquid volume in the collection chamber 1 is constant, the flow rate during a given cycle is inversely proportional to the length of the cycle. As the rate of gas flow decreases, the time interval during which the vacuum source is disconnected from the collection chamber 1, i.e. the length of the cycle, increases proportionately. This is because the time interval during which the vacuum source is disconnected from the collection chamber is the time that it takes the pressure in the chamber to increase from the predetermined first threshold $P_1$ to the second predetermined threshold $P_2$. This increase in pressure will occur over a longer period of time if the rate of flow of gas from the patient's pleural cavity is low and will occur over a shorter period of time if the rate of flow of gas from the patient's pleural cavity is high. Thus, the length of the cycle is a measure of flow rate, and the inverse proportionality between the flow rate and the length of the cycle provides an alternate method of determining a flow rate when the volume of gas in the collection chamber is constant.

In use, the outer end of connecting tube 6 is attached to a thoracic catheter (not shown) which, in turn, is inserted in the patient's pleural cavity; the other end of tube is attached to the chest drainage unit so as to communicate with the collection chamber 1. Connecting tube 7, which also communicates with the collection chamber, is connected to a suitable source of suction such as a hospital suction source. When the chest drainage apparatus is turned on, suction is applied through the collection chamber to the patient's pleural cavity. Both liquid and gases sucked from the pleural cavity will enter the collection chamber 1 through connecting tube 6. The liquid, e.g. blood, will drop to the bottom of the chamber, while the gases suctioned from the cavity will travel across the upper portion of the chamber and out through the suction source.

The microcomputer controller receives inputs from the pressure transducer and the liquid volume sensor. When the pressure in the collection chamber falls below a predetermined threshold which is input into the microcomputer controller prior to operation of the unit, a signal is sent to the solenoid which closes the control valve, thus shutting off the vacuum source. As gases are drawn from the patient's pleural cavity, the pressure in the collection chamber 1 will gradually increase until it exceeds a second predetermined threshold. When this occurs, the control valve is opened, re-establishing communication between the vacuum source and the collection chamber.

The display panel 4 continuously receives input from the microcomputer controller 2 and displays the calculated flow or leakage rate, the vacuum level, the liquid drainage volume in the collection chamber, the time the chest drainage unit was in operation, and the time which elapsed since the last determination of flow rate.

The apparatus of the present invention provides essential advantages over prior art chest drainage apparatus, by enabling the rate of leakage from a patient's pleural cavity to be accurately determined at levels which are very low, near or at zero. This capability is essential in monitoring the healing process in patients having air leaks in their lungs. The apparatus of the present invention also eliminates the need for a high-gain, high-stability disposable amplifier circuit for a direct gas flow sensor and for a disposable mechanical vacuum regulator to be used in connection with the chest drainage apparatus. The following paper examples illustrate how flow rates are determined in the preferred embodiment of the invention. Alternate embodiments of the invention may also be practiced.

EXAMPLES

The terms and equations below define the parameters used to calculate flow rate in the following examples.

| Terms and Equations | Units |
|---|---|
| $V_T$: total CDU volume = 3000 | ml |
| $P_A$: ambient (atmospheric) pressure = 950 | cm $H_2O$ absolute |
| $P_B$: suction set point at beginning of cycle (adjustable) | cm $H_2O$ relative to ambient |
| $P_C$: suction set point at completion of cycle (factory fixed to $P_B$) | cm $H_2O$ relative to $P_B$ |
| $P_1 = P_A - P_B$ = first threshold pressure | cm $H_2O$ absolute |
| $P_2 = P_A - P_B + P_C$ = second threshold pressure | cm $H_2O$ absolute |
| $C_B$: drainage volume at beginning of cycle | ml |
| $C_C$: drainage volume at completion of cycle | ml |
| $V_1 = V_T - C_B$ = CDU air space at beginning of cycle | ml |
| $V_2 = V_1 (P_A - P_B)/(P_A - P_B + P_C) = V_1 P_1/P_2 = $ theoretical air volume at completion of cycle | ml |
| $V_L = (V_T - V_2 - C_C) P_2/P_A$ = volume of air leaked during cycle, normalized to ambient | ml |
| $T_C$: length of cycle (variable, measured) | sec |
| $R_L = 3600 V_L/T_C$ = rate of aire leakage | ml/hr |

EXAMPLE 1

$P_A$ = 950 cm $H_2O$,
$P_B$ = 25.0 cm $H_2O$,
$P_C$ = (internally regulated at $P_B$ − 1 cm $H_2O$) = 24 cm $H_2O$,
$C_B$ = 0.0 ml,
$C_C$ = 0.5 ml, and
$T_C$ = 0.3 sec.
$V_1 = V_T - C_B$ = 3,000.0 ml − 0 ml = 3,000.0 ml
$V_2$ = 3000 (950−25)/(950−24) = 2996.76 ml
$V_L$ = (3000−2996.76−0.5) (950−24)/950 = 2.671 ml
$R_L$ = (3600 sec/hr) (2.67/ml) (0.3 sec) = 32046 ml/hr

EXAMPLE 2

$P_A$ = 950 cm $H_2O$,
$P_B$ = 25 cm $H_2O$
$P_C$ (internally regulated at $P_B$ − 1 cm $H_2O$) = 24 cm $H_2O$
$C_B$ = 1200 ml
$C_C$ = 1200.2 ml, and
$T_C$ = 15 sec
$V_1 = V_T - C_B$ = 3000 ml − 1200 ml = 1800 ml
$V_2$ = 1800 (950−25)/(950−24) = 1798.06 ml
$V_L$ = (3000−1798.06−1200.2) (950−24)/950 = 1.700 ml
$R_L$ = (3600 sec/hr) (1.70 ml)/15 sec = 407.9 ml/hr

EXAMPLE 3

$P_A$ = 950 cm $H_2O$,
$P_B$ = 25 cm $H_2O$
$P_C$ (internally regulated at $P_B$ − 1 cm $H_2O$) = 24 cm $H_2O$
$C_B$ = 1950
$C_C$ = 19.59.05, and
$T_C$ = 350 sec
$V_1 = V_T 31 C_B$ = 3000 ml = 1050 ml
$V_2$ = 1050 (950−25)/(950−24) = 1048.87 ml
$V_L$ = (3000−1048.87−1950.05) (950−24)/950 = 1.057 ml
$R_L$ = (3600 sec/hr) (1.084 ml)/350 sec = 10.9 ml/hr The pressures referred to in the foregoing description refer to absolute pressure. As is clear to those skilled in the art, the absolute pressures referred to can be easily translated to negative or vacuum pressure commonly referred to where the absolute pressure is lower than ambient air pressure.

What is claimed is:

1. In a chest drainage apparatus having a collection chamber therein for receiving fluid and gas to be drained from a pleural cavity of a patient and a vacuum source for applying suction to said collection chamber, the improvement comprising:
   a pressure transducer for measuring the negative pressure in said collection chamber;
   valve means connecting said chest drainage unit to said vacuum source;
   means responsive to said pressure transducer for causing said vacuum source to the connected to said chest drainage unit when the negative pressure in said collection chamber is less than or equal to a first predetermined threshold and for causing said vacuum source to be disconnected from said chest drainage unit when the negative pressure in said collection chamber equals or exceeds a second predetermined threshold; and
   means for measuring the time period during which said vacuum source is disconnected from said chest drainage unit and means for determining the rate of flow of gas into said collection chamber.

2. An apparatus as claimed in claim 1, further comprising means for adjusting said first threshold and said second threshold.

3. An apparatus as claimed in claim 2, further comprising means for adjusting said first threshold to a value defined relative to ambient pressure or to said second threshold.

4. An apparatus as claimed in claim 2, further comprising means for adjusting said second threshold to a value defined relative to ambient pressure or to said first threshold.

5. An apparatus as claimed in claim 1, wherein said chest drainage unit is connected to and disconnected from said vacuum source by means of a control valve regulated by a solenoid.

6. A chest drainage apparatus as claimed in claim 1, further comprising means for continuously displaying one or more of the following; the rate of flow of gas into said collection chamber, the gas pressure in the collection chamber, the liquid drainage volume in said collection chamber, and the time which elapsed since operation of said chest drainage unit began.

7. In a chest drainage apparatus having a collection chamber therein for receiving fluid and gas to be drained from a pleural cavity and a vacuum source for applying suction to said collection chamber, an improvement comprising:
 a pressure transducer for measuring the negative pressure in said collection chamber;
 valve means connecting said chest drainage unit to said vacuum source;
 means responsive to said pressure transducer for causing said vacuum source to be connected to said chest drainage unit when the negative pressure in said collection chamber is less than or equal to a first predetermined threshold and for causing said vacuum source to be disconnected from said chest drainage unit when the negative pressure in said collection chamber equals or exceeds a second predetermined threshold;
 means for measuring the time period during which said vacuum source is disconnected from said chest drainage unit and indicating the rate of flow of gas into said collection chamber; and
 further comprising means for correcting the measured gas volume at the end of each period during which said vacuum source is disconnected, so that said gas volume does not reflect any decrease in volume during said period caused by the flow liquid into said collection chamber, but reflects only increases in volume during said period caused by the flow of gas from said pleural cavity into said collection chamber.

* * * * *